(12) United States Patent
Ekwuribe et al.

(10) Patent No.: US 6,593,492 B1
(45) Date of Patent: Jul. 15, 2003

(54) RESOLUTION OF INTERMEDIATES IN THE SYNTHESIS OF SUBSTANTIALLY PURE BICALUTAMIDE

(75) Inventors: Nnochiri Nkem Ekwuribe, Cary, NC (US); Kenneth D. James, Mebane, NC (US)

(73) Assignee: Nobex Corporation, Durham, NC (US)

( * ) Notice: Subject to any disclaimer, the term of this patent is extended or adjusted under 35 U.S.C. 154(b) by 135 days.

(21) Appl. No.: 09/695,884

(22) Filed: Oct. 25, 2000

Related U.S. Application Data

(60) Provisional application No. 60/161,884, filed on Oct. 27, 1999.

(51) Int. Cl.⁷ .............................................. C07C 67/02
(52) U.S. Cl. ...................................................... 560/250
(58) Field of Search .......................................... 560/250

(56) References Cited

U.S. PATENT DOCUMENTS

| | | | | |
|---|---|---|---|---|
| 4,636,505 A | * | 1/1987 | Tucker | |
| 4,880,839 A | * | 11/1989 | Tucker | |
| 5,985,868 A | | 11/1999 | Gray | .......................... 514/220 |

FOREIGN PATENT DOCUMENTS

| | | | | |
|---|---|---|---|---|
| WO | WO 94/08986 | 4/1994 | ......... | C07D/311/22 |
| WO | WO 95/19770 | 7/1995 | ......... | A61K/31/275 |
| WO | WO 98/55153 | 12/1998 | ......... | A61K/49/04 |

OTHER PUBLICATIONS

WO 95/19770. Gray (1995). Methods and compositions for treating androgen–dependent diseases using optically pure R–(–)–casodex.*

Tucker et al., "Resolution of the Nonsteroidal Antiandrogen 4'–Cyano–3–[(4–fluorophenyl)sulfonyl] – 2 – hydroxy –2– methyl–3'–(trifluoromethyl)–propionanilide and the Determination of the Absolute Configuration of the Active Enantiomer," *J. Med. Chem.*, 31:4 885–887 (1988).

International Search Report corresponding to International Application No. PCT/US00/41609; mailed Apr. 12, 2001.

* cited by examiner

*Primary Examiner*—Ralph Gitomer

(74) *Attorney, Agent, or Firm*—Myers Bigel Sibley & Sajovec, P.A.; William A. Barrett, Esq.

(57) ABSTRACT

A methods of preparing a substantially pure enantiomer of an acylanilide such as Casodex® (bicalutamide) and/or its derivatives includes resolving an intermediate compound having the structure of Formula I:

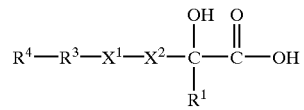

Formula I wherein
  $R^1$ is alkyl or haloalkyl having up to 4 carbons;
  $R^2$ is alkyl having up to 6 carbon atoms;
  $R^3$ is a direct link or alkyl having up to 6 carbon atoms;
  $R^4$ is alkyl, alkenyl, hydroxyalkyl or cycloalkyl each of up to 6 carbons; or $R^4$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^4$ is naphthyl; or $R^4$ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents; and
  $X^1$ is oxygen, sulfur, sulphinyl (—SO—), sulphonyl (—SO₂—), imino (—NH—) or alkylimino (—NR⁵—) where $R^5$ is alkyl having up to 6 carbon atoms.

The resolved intermediate compound of Formula I is then treated under conditions sufficient to provide a substantially pure enantiomer of an acylanilide such as Casodex® (bicalutamide) and/or its derivatives.

21 Claims, 3 Drawing Sheets

RESOLUTION OF INTERMEDIATES IN THE SYNTHESIS OF SUBSTANTIALLY PURE BICALUTAMIDE

RELATED APPLICATIONS

This application claims priority from N. Ekwuribe, U.S. Provisional Application No. 60/161,884, filed Oct. 27, 1999, the disclosure of which is incorporated by reference herein in its entirety.

FIELD OF THE INVENTION

The present invention relates to methods of resolving optically active organic compounds, and more particularly to methods of resolving optically active pharmaceutical compounds.

BACKGROUND OF THE INVENTION

Androgen deprivation is a common treatment for persons with prostate cancer. Various non-steroidal antiandrogens are known for use in the treatment of prostate cancer. For example, bicalutamide, which may be among the most commonly used non-steroidal antiandrogens in the world, is typically used in the treatment of prostate cancer. Bicalutamide is commercially available as Casodex® (bicalutamide) from Astra Zeneca Pharmaceuticals.

The chemical name of bicalutamide is N-[4-cyano-3-(trifluoromethyl)phenyl]-3-[(4-fluorophenyl)sulfonyl]-2-hydroxy-2-methyl-propanamide,(+−). The structural formula of bicalutamide is:

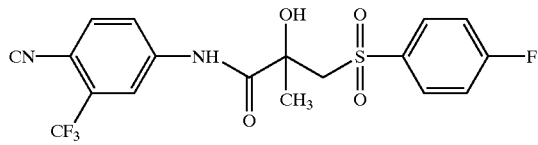

The β-carbon atom in the propanamide is a chiral carbon. As a result, bicalutamide is an optically active compound.

Optically active compounds have the ability to rotate the plane of polarized light. In describing an optically active compound, the prefixes D and L or R and S are used to denote the absolute configuration of the molecule about its chiral center(s). The prefixes d and l or (+) and (−) are used to denote the optical rotation of the compound (i.e., the direction in which a plane of polarized light is rotated by the optically active compound). The l or (−) prefix indicates that the compound is levorotatory (i.e., rotates the plane of polarized light to the left or counterclockwise) while the d or (+) prefix means that the compound is dextrarotatory (i.e., rotates the plane of polarized light to the right or clockwise). The sign of optical rotation, (−) and (+), is not related to the absolute configuration of the molecule, R and S.

Optically active compounds, such as bicalutamide, exist as a pair of stereoisomers that are identical with the notable exception that they are non-superimposable mirror images of one another. A specific stereoisomer, such as the R isomer, may be referred to as an enantiomer. A mixture of R and S enantiomers may be referred to as a racemic mixture.

Bicalutamide, is presently commercially available as a racemic mixture. The racemic mixture of bicalutamide may be synthesized by various methods including, for example, the methods described in U.S. Pat. No. 4,636,505 to Tucker. Tucker further describes various derivatives and analogs of bicalutamide having antiandrogenic properties. Additionally, Tucker states that this racemic mixture of acylanilide derivatives may be resolved into optically active forms which possess antiandrogenic activity. This method requires complete synthesis of the drug in a racemic mixture followed by esterification, resolution of the diastereomers and hydrolysis to obtain the desired enantiomer. Tucker fails to propose specific methods for achieving this resolution.

U.S. Pat. No. 5,985,868 to Gray proposes synthesizing racemic mixtures of Casodex® (bicalutamide) using methods as described in U.S. Pat. No. 4,636,505 to Tucker, and obtaining the (R)-(−) enantiomer of Casodex® (bicalutamide) by resolution of the enantiomers of Casodex® (bicalutamide) using fractional crystallization or chromatography of diastereomeric esters of chiral acids. Gray notes that other standard methods of resolution such as simple crystallization and chromatographic resolution can also be used. The methods of Gray require complete synthesis of the drug in a racemic mixture. The racemic mixture of the drug is then modified to facilitate resolution, and modified again to yield the active enantiomeric compound. Gray further states that intermediates of Casodex® (bicalutamide) may be resolved using fractional crystallization or chromatography of diastereomeric esters of chiral acids. However, Gray fails to propose specific intermediates, specific methods, specific esters, and/or specific chiral acids for accomplishing such a resolution. Gray further states that a carboxylic acid precursor, 3-(4-fluorophenyl)-2-hydroxy-2-methylpropanoic acid, which has the following structure:

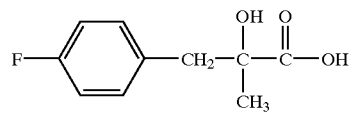

may be resolved by fractional crystallization of diastereomeric salts with chiral amines. However, Gray fails to propose specific methods, specific diastereomeric salts, and/or specific chiral amines for accomplishing such a resolution.

In Howard Tucker et al., *Resolution of the Nonsteroidal Antiandrogen 4'-Cyano-3-[(4-fluorophenyl)sulfonyl]-2-hydroxy-2-methyl-3'-(trifluoromethyl)-propioanilide and the Determination of the Absolute Configuration of the Active Enantiomer*, 31 J. Med. Chem. 885–887 (1988), the authors propose preparing chiral bicalutamide by resolution of the thioether:

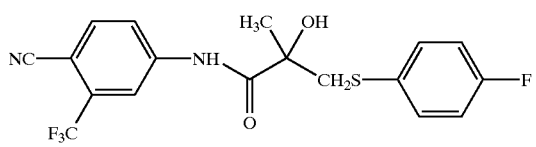

Once resolved, the enantiomers of the thioether may be oxidized to the sulfone by known means. The authors also propose resolution of the thioether by reaction of the thio ether with (R)-(−)-camphanoyl chloride in pyridine to provide the diastereomeric ester:

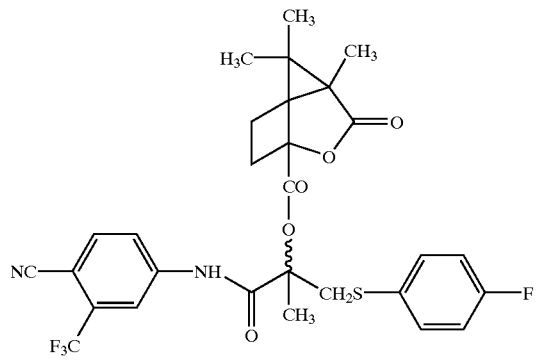

The diastereomeric esters may then be separated by careful flash chromatography on silica gel. The individual pure diasteriomeric isomers may then be hydrolyzed, without racemization, using methanolic sodium hydroxide to yield enantiomeric alcohols:

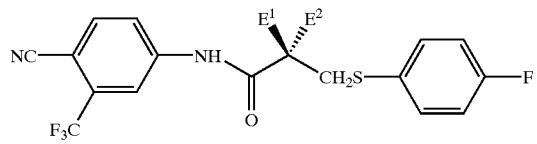

wherein $E^1$ is $CH_3$ and $E^2$ is OH for the S configuration, or $E^1$ is OH and $E^2$ is $CH_3$ for the R configuration. These methods require complete synthesis of the drug in a racemic mixture. The racemic mixture of the drug is then modified to facilitate resolution, and modified again to yield the active enantiomeric compound.

Synthesis of the entire drug prior to resolution may result in time and labor costs required for the performance of extra steps, and in the inefficient use of costly starting materials that become components of the less preferred S-enantiomer, which may be disposed of or recycled, resulting in even more expense. Consequently, there is a need in the art for a more streamlined method for preparing substantially enantiomerically pure bicalutamide, which eliminates these additional steps, and which makes efficient use of the starting materials and minimizes waste.

SUMMARY OF THE INVENTION

Embodiments of the present invention provide a synthetic method comprising a resolution step which takes place prior to the addition of the most expensive components of the active compound. By resolving an intermediate compound rather than resolving the completely synthesized drug as described above for conventional methods, methods according to the present invention may reduce or eliminate the need for additional post-synthesis procedures and/or reduce or eliminate the need to recycle the less-preferred enantiomer. Additionally, the use of expensive starting materials such as:

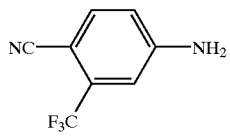

to produce the less-preferred enantiomer may be avoided, which may reduce the costs of producing a substantially pure form of the more-preferred enantiomer.

According to embodiments of the present invention, methods of preparing a substantially pure enantiomer of an acylanilide such as Casodex® (bicalutamide) and/or its derivatives are provided. The methods include resolving an intermediate compound having the structure of Formula I:

Formula I

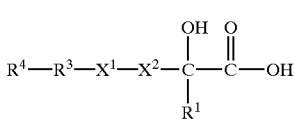

wherein $R^1$ is alkyl or haloalkyl having up to 4 carbons;

$R^2$ is alkyl having up to 6 carbon atoms;

$R^3$ is a direct link or alkyl having up to 6 carbon atoms;

$R^4$ is alkyl, alkenyl, hydroxyalkyl or cycloalkyl each of up to 6 carbons; or $R^4$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^4$ is naphthyl; or $R^4$ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents; and $X^1$ is oxygen, sulfur, sulphinyl (—SO—), sulphonyl (—SO$_2$—), imino (—NH—) or alkylimino (—NR$^5$—) where $R^5$ is alkyl having up to 6 carbon atoms.

The resolved intermediate compound of Formula I is then treated under conditions sufficient to provide a substantially pure enantiomer of the acylanilide.

In some embodiments of the present invention, the step of resolving an intermediate compound of Formula I includes crystallizationally resolving the intermediate compound of Formula I. The crystallizationally resolving step includes contacting the intermediate compound of Formula I with a chiral base to provide a diastereomeric mixture of a chiral salt, crystallizationally resolving the diastereomeric mixture of the chiral salt to provide a substantially pure enantiomer of the chiral salt, and recovering a substantially pure enantiomer of the intermediate compound of Formula I. The contacting step preferably includes contacting the intermediate compound of Formula I with (−)-cinchonidine to provide a diastereomeric mixture of the chiral salt. The step of crystallizationally resolving the diastereomeric mixture of the chiral salt preferably includes contacting the diastereomeric mixture of the chiral salt with a solvent system comprising, for example, methylene chloride and diethyl ether. In other embodiments, the step of resolving an intermediate compound of Formula I may include high performance liquid chromatographically resolving the intermediate compound of Formula I.

The resolved intermediate is preferably contacted with an aniline compound having the structure of Formula II:

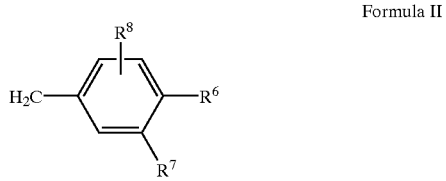

Formula II wherein

R$^6$ is cyano, carbamoyl, nitro, fluoro, chloro, bromo, iodo, or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms, or phenylthio, phenylsulphinyl or phenylsulphonyl;

R$^7$ is cyano, carbamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of having up to 4 carbon atoms; or phenylthio, phenylsulphinyl or phenylsulphonyl; and R$^8$ is hydrogen or halogen;

under conditions sufficient to provide a substantially pure enantiomer of an acylanilide. The substantially pure enantiomer of the acylanilide is preferably the (R)-enantiomer of Casodex® (bicalutamide).

By resolving intermediates rather than resolving completely synthesized drugs, methods according to the present invention may provide more cost effective ways of synthesizing substantially pure enantiomers of acylanilides such as Casodex® (bicalutamide) and derivatives thereof than are provided by conventional resolution techniques. For example, methods according to the present invention may be more cost effective because they resolve the intermediates prior to reacting them with the expensive aniline component, avoiding unwanted costs associated with the expensive aniline component, which is typically wasted in the production of the less-preferred enantiomer.

DETAILED DESCRIPTION OF PREFERRED EMBODIMENTS

Figure 1:
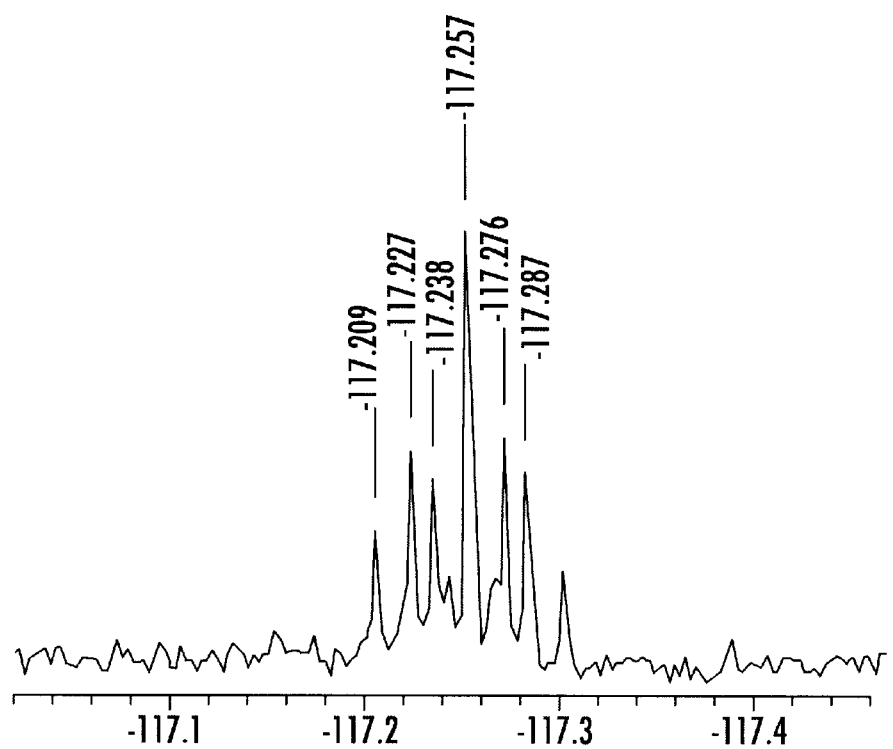
FIG. 1 shows a $^{19}$F NMR spectrum of the pure salt of the (R)-hydroxyacid and (−)-cinchonidine.

The invention will now be described with respect to preferred embodiments described herein. It should be appreciated however that these embodiments are for the purpose of illustrating the invention, and are not to be construed as limiting the scope of the invention as defined by the claims. As the substituents R$^1$–R$^8$ and X$^1$ have been defined above, they will not be further defined herein other than to describe preferred substituents for the preferred embodiments. Unless otherwise noted, all percentages used herein are percent by weight. As used herein, the term "substantially enantiomerically pure" refers to a substance that has preferably between about 95% and 100% of one form (either R or S) and between about 5% and 0% of the other form, more preferably between about 99% and 100% of one form (either R or S) and between about 1% and 0% of the other form, and, most preferably, between about 99.9% and 100% of one form (either R or S) and about 0.1% and 0% of the other form.

Embodiments of the present invention provide methods of preparing a substantially pure enantiomer of an acylanilide. Particularly preferred methods according to the present invention resolve a racemic mixture of intermediate compounds to provide Casodex® (bicalutamide) and/or its derivatives in a more cost effective manner than conventional methods that resolve the racemic mixture of Casodex® (bicalutamide) and/or its derivatives.

According to embodiments of the present invention, methods of preparing a substantially pure enantiomer of an acylanilide such as Casodex® (bicalutamide) and/or its derivatives are provided. The methods include resolving an intermediate compound having the structure of Formula I:

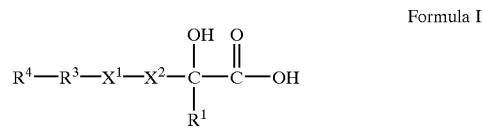

Formula I

The resolved intermediate compound of Formula I is then treated under conditions sufficient to provide a substantially pure enantiomer of the acylanilide. Preferably, R$^1$ is lower alkyl having up to 4 carbons, and R$^2$ is lower alkyl having up to 6 carbons. More preferably, R$^1$ is methyl and R$^2$ is methylene. R$^3$ is preferably a direct link (i.e., one or more bonds between X$^1$ and R$^4$). R$^4$ is preferably phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl. More preferably, R$^4$ is phenyl which bears one, two or three substituents independently selected from hydrogen and halogen. Most preferably, R$^4$ is 4-fluorophenyl. Preferably, X$^1$ is sulfur, sulphinyl, sulphonyl or imino. X$^1$ is more preferably sulfur, sulphinyl, or sulphonyl and is most preferably sulfur. The intermediate compounds according to the present invention may be prepared by various methods as will be understood by those skilled in the art. Exemplary methods of preparing particularly preferred intermediate compounds are described hereinbelow.

According to preferred embodiments of the present invention, a racemic mixture of the intermediate compound of Formula I is crystallizationally resolved. The intermediate compound of Formula I is contacted with a chiral base to obtain a diastereomeric mixture of chiral salts. The chiral salts of the diastereomeric mixture are then selectively crystallized to resolve the chiral salts into (R)- and (S)-salt enantiomers. The more preferred salt enantiomer is then treated to recover the more preferred hydroxyacid.

The chiral base is preferably (−)-cinchonidine. More preferably, the chiral base is (−)-cinchonidine (96%), which is commercially available from Aldrich of Milwaukee, Wis. While the chiral base is preferably (−)-cinchonidine, other chiral bases may be employed including, but not limited to, brucine.

In particularly preferred embodiments, the substantially pure enantiomer of the more preferred (R)-hydroxyacid is resolved as follows:

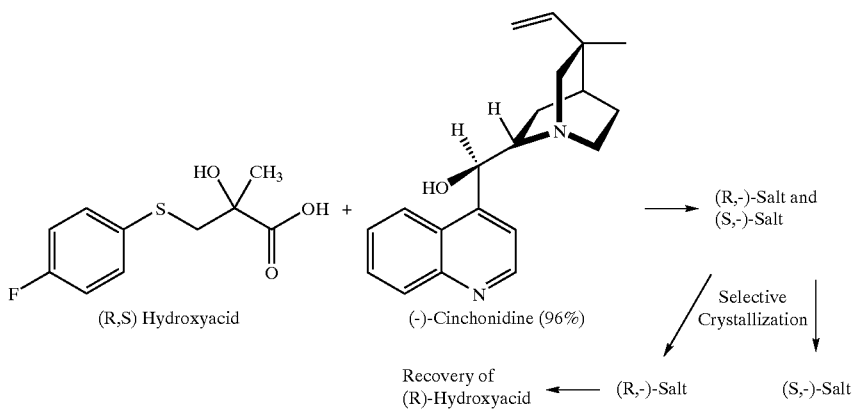

The selective crystallization is preferably performed by contacting the diastereomeric mixture of the (R,–)-salt and the (S,–)-salt with a solvent system. The solvent system preferably includes methylene chloride and diethyl ether. The methylene chloride/diethyl ether solvent system preferably includes between about 1 and 40 percent by volume methylene chloride and between about 60 and 99 percent by volume diethyl ether, more preferably includes between about 5 and 30 percent by volume methylene chloride and between about 70 and 95 percent by volume diethyl ether, and most preferably includes between about 10 and 20 percent by volume methylene chloride and between about 80 and about 90 percent by volume diethyl ether. A particularly preferred solvent system consists essentially of between about 10 and 20 percent by volume methylene chloride and between about 80 and 90 percent by volume diethyl ether.

Figure 2:
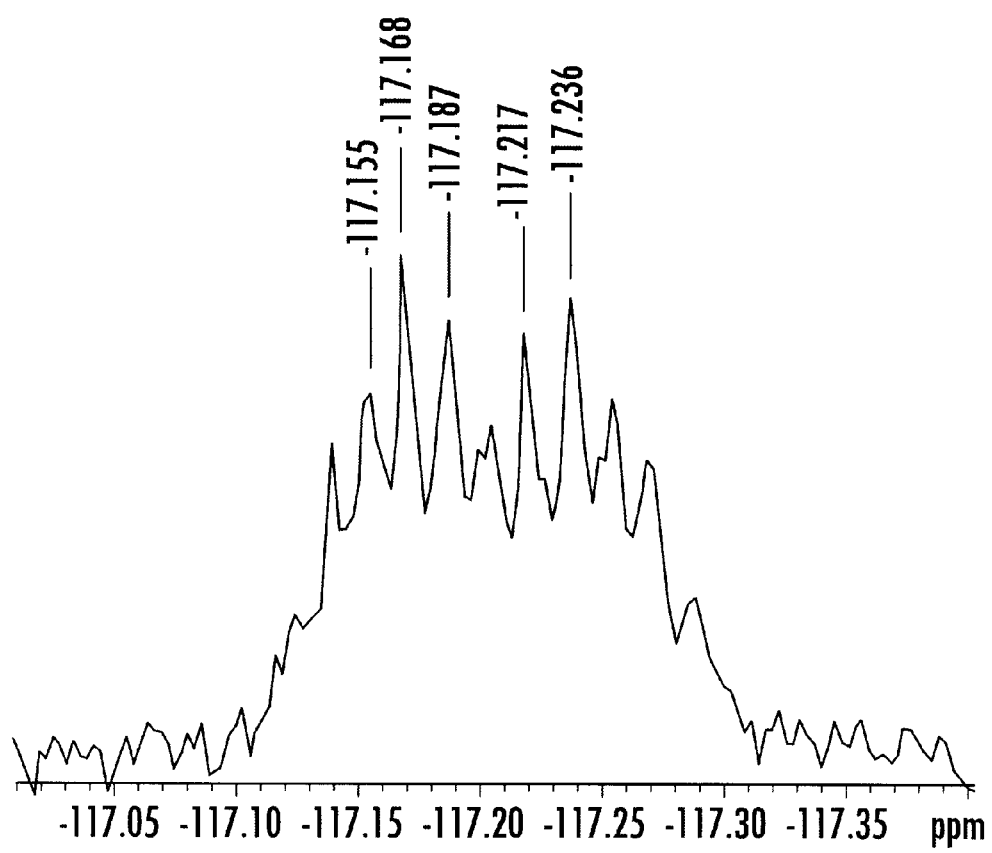
FIG. 2 shows a $^{19}$F NMR spectrum of the salt of the racemic (R,S)-hydroxyacid and (−)-cinchonidine prior to resolution.
Figure 3:
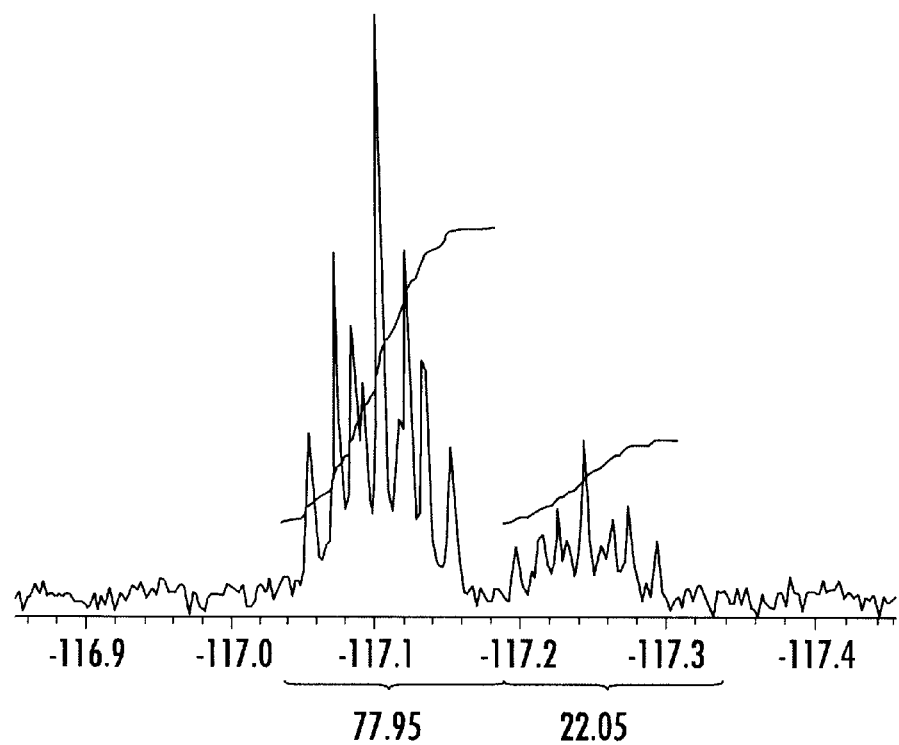
FIG. 3 shows a $^{19}$F NMR spectrum of the salt of the racemic (R,S)-hydroxyacid and (−)-cinchonidine after one round of crystallization.

Progress of the resolution may be monitored by $^{19}$F NMR analysis, as illustrated in FIGS. 1 through 3. FIG. 1 shows a $^{19}$F NMR spectrum of the pure salt of the (R)-hydroxyacid and (–)-cinchonidine. This (R)-hydroxyacid was made by asymmetric synthesis as described in the co-pending and co-assigned application entitled "Methods of Asymmetrically Synthesizing Enantiomers of Casodex, Its Derivatives and Intermediates Thereof" to Nnochiri N. Ekwuribe. This spectrum was used as a standard for comparison in determining the resolution of the racemic mixture. FIG. 2 shows a $^{19}$F NMR spectrum of the salt of the racemic (R,S)-hydroxyacid and (–)-cinchonidine prior to resolution. The left portion of the signal is from the (S)-hydroxyacid and the right portion of the signal is from the (R)-hydroxyacid. FIG. 3 shows a $^{19}$F NMR spectrum of the salt of the racemic (R,S)-hydroxyacid and (–)-cinchonidine after one round of crystallization. This spectrum illustrates that approximately 78% of the crystals formed were the cinchonidine salt of the (S)-hydroxyacid. Thus, the solution was becoming enriched with the salt of the more preferred (R)-hydroxyacid.

While those skilled in the art will understand how to recover the intermediate compound from the salt, the (R)-intermediate compound (e.g., (R)-hydroxyacid) is preferably recovered from the salt by acidification with aqueous 1M HCl followed by extraction with an organic solvent, such as methylene chloride or ethyl acetate.

According to another aspect of the present invention, the intermediate compound of Formula I may be separated by various means for physico-chemical separation known in the art, such as chromatographic resolution. Exemplary methods may be found in G. Subramanian, *A Practical Approach to Chiral Separations by Liquid Chromatography*, John Wiley & Sons, 1994; Thomas E. Beesley, Raymond P. W. Scoff, *Chiral Chromatography*, John Wiley & Son Ltd., 1999; and Satinder Ahuja, *Chiral Separations: Applications and Technology*, American Chemical Society, 1996. In a preferred method, the intermediates are separated using high pressure liquid chromatography (HPLC) by methods such as those described in Krstulovic, A. M., ed. *Chiral Separations by HPLC: Applications to Pharmacological Compounds*, Halsted Press, 1989. One skilled in the art will understand how to chromatographically resolve the intermediate compounds described herein.

In preferred embodiments, the intermediate compound has the structure of Formula III:

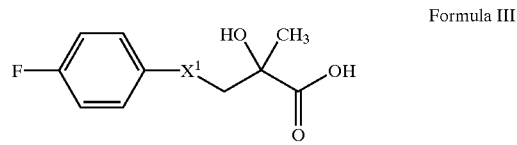

Formula III wherein $X^1$ is sulfur or sulphonyl. The intermediate compounds of Formula III may be prepared by various methods as will be understood by those skilled in the art. For example, the intermediate compounds of Formula III may be prepared according to methods described in Howard Tucker et al., *Resolution of the Nonsteroidal Antiandrogen 4'-Cyano-3-[(4-fluorophenyl)sulfonyl]-2-hydroxy-2-methyl-3'-(trifluoromethyl)-propioanilide and the Determination of the Absolute Configuration of the Active Enantiomer*, 31 J. Med. Chem. 885–887 (1988), the disclosure of which is incorporated herein in its entirety. As another example, the intermediate compounds of Formula III may be prepared from the compound of Formula IV:

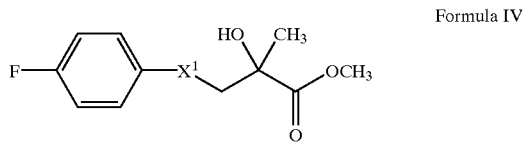

Formula IV wherein $X^1$ is sulfur or sulphonyl. Hydrolysis of the compound of Formula IV will yield the compound of Formula III. When $X^1$ is sulfur, the compound may further be oxidized to provide a compound where $X^1$ is sulphonyl.

As still another example, the intermediate compounds of Formula III may be prepared using commercially available compounds as follows:

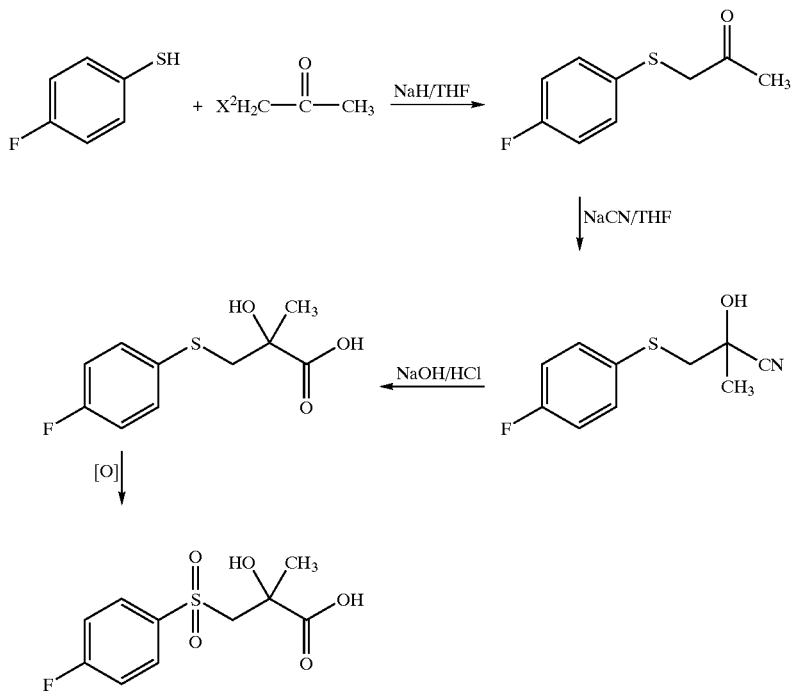

wherein $X^2$ is a leaving group, preferably chloro, bromo, or iodo; NaH is sodium hydride; THF is tetrahydrofuran; and [O] is an oxidizing agent as will be understood by those skilled in the art.

As yet another example, the intermediate compound of Formula III may be prepared using commercially available materials as follows:

wherein mCPBA is meta-chloroperbenzoic acid, and hydrolysis is preferably performed using an aqueous acid or aqueous base solution. A racemic mixture of the intermediate compound of Formula III may be resolved according to methods of the present invention described above.

Once the more preferred substantially pure enantiomer of the intermediate compound of Formula I or III has been

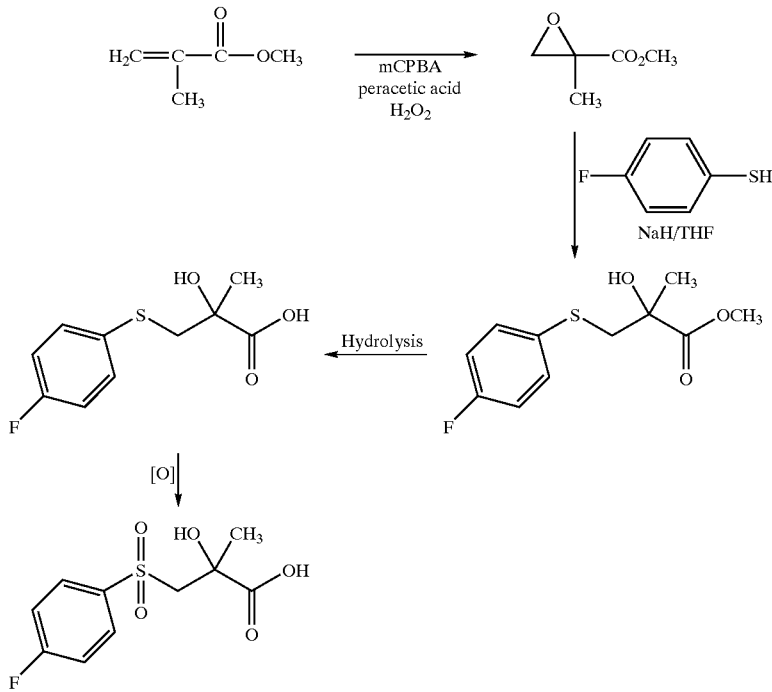

prepared by resolution as described above, the compound may be contacted with the aniline compound of Formula II:

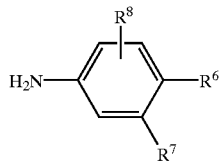

Formula II to provide the more preferred substantially pure enantiomer of the acylanilide. $R^6$ is preferably cyano, fluoro, chloro, bromo, iodo, or hydrogen. More preferably, $R^6$ is cyano, fluoro, chloro, bromo, iodo, and, most preferably, $R^6$ is cyano. $R^7$ is preferably perfluoroalkyl, perfluoroalkylthio, perfluoroalkylsulphinyl or perfluoroalkylsulphonyl each of having up to 4 carbon atoms. More preferably, $R^7$ is perfluoroalkyl, and, most preferably, $R^7$ is perfluoromethyl. Most preferably, $R^8$ is hydrogen.

By resolving the racemic mixture of the intermediate compounds prior to synthesizing the intermediate with the more expensive aniline compound, methods according to the present invention may provide more cost effective ways of preparing substantially pure enantiomers of acylanilides such as Casodex® (bicalutamide) and/or derivatives thereof.

The present invention will now be described with reference to the following example. It should be appreciated that this example is for the purposes of illustrating aspects of the present invention, and does not limit the scope of the invention as defined by the claims.

EXAMPLE

Formation of the Salt

The salt of the (R,S)-hydroxyacid and (−)-cinchonidine was formed by mixing a solution of the hydroxyacid (one equivalent) with a solution of (−)-cinchonidine (one equivalent). Cinchonidine was generally dissolved in chloroform, but the hydroxyacid may have been dissolved in solvents such as chloroform, methylene chloride, ethyl acetate, or ethanol. The mixture was then stirred overnight at room temperature. After removal of the solvent by rotary evaporation, the residual salt was then redissolved in the desired recrystallization solvent.

Recrystallization

A typical procedure involved placing 20 mg of the salt of the (R,S)-hydroxyacid and (−)-cinchonidine in a vial. Ethyl ether (2 mL) was then added. Methylene chloride was then added dropwise (with occasional shaking) just until the salt had been solubilized. The solution was then placed at 4° C. for crystallization.

Assaying Resolution

After crystallization had occurred, the supernatant was removed. The crystals were then dissolved in deuterated chloroform ($CDCl_3$). The ratio of (R)- to (S)-enantiomer could then be assayed by integration of the fluorine signal(s) using $^{19}F$ NMR.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method of preparing a substantially pure enantiomer of an acylanilide comprising:

(a) contacting an intermediate compound having the structure of Formula I:

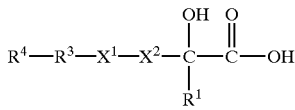

Formula I wherein
    $R^1$ is alkyl or haloalkyl having up to 4 carbons;
    $R^2$ is alkyl having up to 6 carbon atoms;
    $R^3$ is a direct link or alkyl having up to 6 carbon atoms;
    $R^4$ is alkyl, alkenyl, hydroxyalkyl or cycloalkyl each of up to 6 carbons; or $R^4$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^4$ is naphthyl; or $R^4$ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents; and
    $X^1$ is oxygen, sulfur, sulphinyl (—SO—), sulphonyl (—$SO_2$—), imino (—NH—) or alkylimino (—$NR^5$—) where $R^5$ is alkyl having up to 6 carbon atoms,
    with (−)-cinchonidine to provide a diastereomeric mixture of intermediate compound-cinchonidine chiral salts;

(b) contacting the diastereomeric mixture of the intermediate compound-cinchonidine chiral salts with a solvent system comprising between about 1 and 40 percent by volume methylene chloride and between about 60 and 99 percent by volume diethyl ether to provide a substantially pure enantiomer of the intermediate compound-cinchonidine chiral salt;

(c) recovering a substantially pure enantiomer of the intermediate compound of Formula I; and (d) treating the substantially pure enantiomer of the intermediate compound of Formula I under conditions sufficient to provide a substantially pure enantiomer of an acylanilide.

2. The method according to claim 1, wherein the solvent system consists essentially of between about 10 and 20 percent by volume methylene chloride and between about 80 and 90 percent by volume diethyl ether.

3. The method according to claim 1, wherein $R^1$ is alkyl having up to 4 carbons; $R^2$ is alkyl having up to 6 carbons; $R^3$ is a direct link; $R^4$ is phenyl having one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; and $X^1$ is sulfur, sulphinyl, sulphonyl or imino.

4. The method according to claim 1, wherein $R^1$ is methyl, $R^2$ is methylene, $R^3$ is a direct link, $R^4$ is 4-fluorophenyl, and $X^1$ is sulfur, sulphinyl, or sulphonyl.

5. the method according to claim 4, wherein the solvent system consists essentially of between 10 and 20 percent by volume methylene chloride and between about 80 and 90 percent by volume diethyl ether.

6. The method according to claim 1, wherein step (d) comprises contacting the substantially pure enantiomer of the intermediate with an aniline compound having the structure of Formula II:

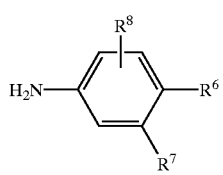

Formula II wherein $R^6$ is cyano, carbamoyl, nitro, fluoro, chloro, bromo, iodo, or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms, or phenylthio, phenylsulphinyl or phenylsulphonyl;

$R^7$ is cyano, carbamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of having up to 4 carbon atoms; or phenylthio, phenylsulphinyl or phenylsulphonyl; and $R^8$ is hydrogen or halogen;

under conditions sufficient to provide a substantially pure enantiomer of an acylanilide.

7. The method according to claim 6, wherein $R^6$ is cyano, $R^7$ is perfluoromethyl, and $R^8$ is hydrogen.

8. The method according to claim 7, wherein the solvent system consists essentially of between about 10 and 20 percent by volume methylene chloride and between about 80 and 90 percent by volume diethyl ether.

9. The method according to claim 6, wherein the solvent system consists essentially of between about 10 and 20 percent by volume methylene chloride and between about 80 and 90 percent by volume diethyl ether.

10. The method according to claim 1, wherein $R^4$ is phenyl having one, two or three substituents independently selected from hydrogen, halogen, nitro, carboxy, carbamoyl, cyano, alkyl, alkoxy, alkanoyl, alkylthio, alkylsulphinyl, alkylsulphonyl, and perfluoroalkyl; and $X^1$ is sulfur, sulphinyl, sulphonyl or imino.

11. The method according to claim 10, wherein the solvent system consists essentially of between about 10 and 20 percent by volume methylene chloride and between about 80 and 90 percent by volume diethyl ether.

12. A method of preparing a substantially pure enantiomer of Casodex® (bicalutamide) or a derivative thereof comprising:

(a) contacting an intermediate compound having the structure of Formula I:

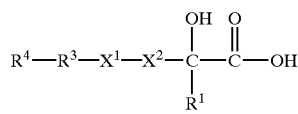

Formula I wherein
$R^1$ is methyl;
$R^2$ is methylene;
$R^3$ is a direct link;
$R^4$ is 4-fluorophenyl; and
$X^1$ is sulfur, sulphinyl (—SO—), or sulphonyl (—SO$_2$—), with (−)-cinchonidine to provide a diastereomeric mixture of intermediate compound-cinchonidine chiral salts;

(b) contacting the diastereomeric mixture of the intermediate compound-cinchonidine chiral salts with a solvent system comprising between about 1 and 40 percent by volume methylene chloride and between about 60 and 99 percent by volume diethyl ether to provide a substantially pure enantiomer of the intermediate compound-cinchonidine chiral salt;

(c) recovering a substantially pure enantiomer of the intermediate compound of Formula I; and (d) treating the substantially pure enantiomer of the intermediate compound of Formula I under conditions sufficient to provide a substantially pure enantiomer of Casodex® (bicalutamide) or a derivative thereof.

13. The method according to claim 12, wherein the solvent system consists essentially of between about 10 and 20 percent by volume methylene chloride and between about 80 and 90 percent by volume diethyl ether.

14. The method according to claim 12, wherein step (d) comprises contacting the resolved intermediate with an aniline compound having the structure of Formula II:

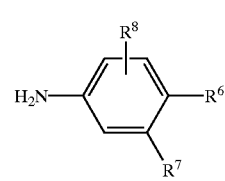

Formula II wherein
$R^6$ is cyano;
$R^7$ is perfluoroalkyl; and
$R^8$ is hydrogen;

under conditions sufficient to provide a substantially pure enantiomer of Casodex® (bicalutamide).

15. A method of preparing a substantially pure enantiomer of an acylanilide comprising:

(a) contacting an intermediate compound having the structure of Formula I:

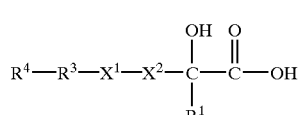

Formula I wherein:
$R^1$ is alkyl having up to 4 carbons;

$R^2$ is alkyl having up to 6 carbon atoms;

$R^3$ is a direct link or alkyl having up to 6 carbon atoms;

$R^4$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; and $X^1$ is sulfur, sulphinyl (—SO—), sulphonyl (—SO$^2$—), with (−)-cinchonidine to provide a diastereomeric mixture of intermediate compound-cinchonidine chiral salts;

(b) contacting the diastereomeric mixture of the intermediate compound-cinchonidine chiral salts with a solvent system comprising between about 1 and 40 percent by volume methylene chloride and between about 60 and 99 percent by volume diethyl ether;

(c) recovering a substantially pure enantiomer of the intermediate compound of Formula I; and (d) treating the substantially pure enantiomer of the intermediate compound of Formula I under conditions sufficient to provide a substantially pure enantiomer of an acylanilide.

16. The method according to claim 15, wherein the solvent system consists essentially of between about 10 and 20 percent by volume methylene chloride and between about 80 and 90 percent by volume diethyl ether.

17. The method according to claim 15, wherein $R^1$ is methyl, $R^2$ is methylene, $R^3$ is a direct link, $R^4$ is 4-fluorophenyl, and $X^1$ is sulfur, sulphinyl, or sulphonyl.

18. The method according to claim 15, wherein step (d) comprises contacting the substantially pure enantiomer of the intermediate with an aniline compound having the structure of Formula II:

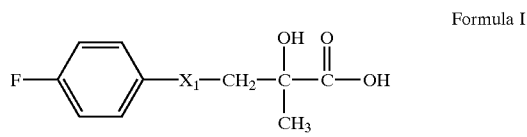

Formula II wherein:

$R^6$ is cyano, carbamoyl, nitro, fluoro, chloro, bromo, iodo, or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms, or phenylthio, phenylsulphinyl or phenylsulphonyl;

$R^7$ is cyano, carbamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of having up to 4 carbon atoms; or phenylthio, phenylsulphinyl or phenylsulphonyl; and $R_8$ is hydrogen or halogen;

under conditions sufficient to provide a substantially pure enantiomer of an acylanilide.

19. The method according to claim 18, wherein $R^6$ is cyano, $R^7$ is perfluoromethyl, and $R^8$ is hydrogen.

20. A method of preparing a substantially pure enantiomer of Casodex® (bicalutamide) or a derivative thereof comprising:

(a) contacting an intermediate compound having the structure of Formula I:

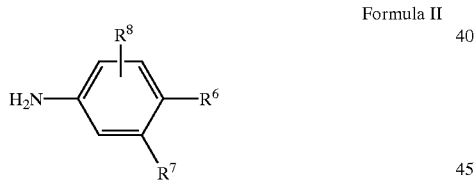

Formula I wherein $X^1$ is sulfur, sulphinyl (—SO—), or sulphonyl (—SO$_2$—), with (−)-cinchonidine to provide a diastereomeric mixture of intermediate compound-cinchonidine chiral salts;

(b) contacting the diastereomeric mixture of the intermediate compound-cinchonidine chiral salts with a solvent system consisting essentially of between about 10 and 20 percent by volume methylene chloride and between about 80 and 90 percent by volume diethyl ether to provide a substantially pure enantiomer of the cinchonidine chiral salt;

(c) recovering a substantially pure enantiomer of the intermediate compound of Formula I; and (d) contacting the resolved intermediate with an aniline compound having the structure of Formula II:

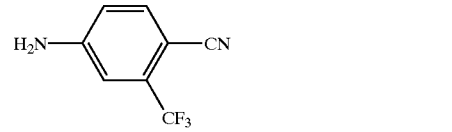

Formula II under conditions sufficient to provide a substantially pure enantiomer of Casodex® (bicalutamide) or a derivative thereof.

21. The method according to claim 20, wherein $X_1$ is sulphonyl, and wherein the contacting of the resolved intermediate with an aniline compound having the structure of Formula II provides a substantially pure enantiomer of Casodex® (bicalutamide).

* * * * *